(12) United States Patent
Lyons et al.

(10) Patent No.: US 6,413,259 B1
(45) Date of Patent: Jul. 2, 2002

(54) BONE PLATE ASSEMBLY INCLUDING A SCREW RETAINING MEMBER

(75) Inventors: Matthew Lyons, Wilbraham, MA (US); Frank La Rosa, Neptune City, NJ (US)

(73) Assignee: Blackstone Medical, Inc, Springfield, MA (US)

( * ) Notice: Subject to any disclaimer, the term of this patent is extended or adjusted under 35 U.S.C. 154(b) by 0 days.

(21) Appl. No.: 09/736,928

(22) Filed: Dec. 14, 2000

(51) Int. Cl.$^7$ ............................................... A61B 17/80
(52) U.S. Cl. ............................ 606/69; 606/70; 606/71; 606/61
(58) Field of Search ..................... 606/71, 69, 70, 606/61; 623/17.11, 17.16

(56) References Cited

U.S. PATENT DOCUMENTS

| | | |
|---|---|---|
| 1,765,239 A | 6/1930 | Meurling |
| 2,401,856 A | 6/1946 | Brock |
| 2,489,870 A | 11/1949 | Dzus |
| 3,023,925 A | 3/1962 | Sher |
| 3,426,364 A | 2/1969 | Lumb |
| 3,534,731 A | 10/1970 | Muller |
| 3,695,259 A | 10/1972 | Yost |
| 3,741,205 A | 6/1973 | Markolf et al. |
| 3,774,244 A | 11/1973 | Walker |
| 4,001,928 A | 1/1977 | Schweiso |
| 4,285,071 A | 8/1981 | Nelson et al. |
| 4,320,421 A | 3/1982 | Larson et al. |
| 4,388,921 A | 6/1983 | Sutter et al. |
| 4,417,571 A | 11/1983 | Nelson et al. |
| 4,484,570 A | 11/1984 | Sutter et al. |
| 4,536,897 A | 8/1985 | Powell |
| 4,563,778 A | 1/1986 | Roche et al. |
| 4,566,138 A | 1/1986 | Lewis et al. |
| 4,599,086 A | 7/1986 | Doty |
| 4,711,234 A | 12/1987 | Vives et al. |
| 4,794,918 A | 1/1989 | Wolter |
| 4,795,468 A | 1/1989 | Hoderek et al. |
| 4,808,185 A | 2/1989 | Peneberg et al. |
| 4,834,752 A | 5/1989 | Van Kampen |
| 4,892,545 A | 1/1990 | Day et al. |
| 4,904,261 A | 2/1990 | Dove et al. |
| 4,917,704 A | 4/1990 | Frey et al. |
| 4,919,666 A | 4/1990 | Buchborn et al. |
| 4,955,325 A | 9/1990 | Zarnowski et al. |
| 4,955,908 A | 9/1990 | Frey et al. |
| 4,973,844 A | 11/1990 | O'Farrell et al. |
| 5,021,062 A | 6/1991 | Adrey et al. |
| 5,041,141 A | 8/1991 | Ypma et al. |
| 5,057,111 A | 10/1991 | Park |
| 5,123,926 A | 6/1992 | Pisharodi |
| 5,147,361 A | 9/1992 | Ojima et al. |
| 5,234,431 A | 8/1993 | Keller |

(List continued on next page.)

FOREIGN PATENT DOCUMENTS

| | | |
|---|---|---|
| CH | 674927 A5 | 8/1990 |
| DE | 29 33 141 | 10/1980 |
| DE | A1 0 313 762 | 8/1988 |
| EP | 0 179 695 A1 | 4/1986 |
| FR | 89 12618 | 9/1989 |
| WO | WO 91/03994 | 4/1991 |
| WO | WO 95/30389 | 11/1995 |
| WO | WO 96/03096 | 2/1996 |
| WO | WO/96/23457 | 8/1996 |

OTHER PUBLICATIONS

Aesculap document "Surgical Technique as described by Ronald I. Appelbaum, M.D." 1999.

*Primary Examiner*—Pedro Philogene
(74) *Attorney, Agent, or Firm*—Dreier & Baritz LLP

(57) ABSTRACT

The present invention is directed to a bone plate assembly including a bone plate, bone screws received in apertures in the assembly, and a screw retaining member fixed to the bone plate which covers at least a portion of the bone screws. When bone screws have been received by the bone plate and inserted into bone and/or tissue, the bone plate assembly can be used to fuse anatomical structures together, such as adjoining bones, or to heal a fracture in bone.

31 Claims, 7 Drawing Sheets

U.S. PATENT DOCUMENTS

| | | |
|---|---|---|
| 5,246,459 A | 9/1993 | Elias |
| 5,261,910 A | 11/1993 | Warden et al. |
| 5,263,987 A | 11/1993 | Shah |
| 5,269,784 A | 12/1993 | Mast |
| 5,282,864 A | 2/1994 | Noiles et al. |
| 5,330,535 A | 7/1994 | Moser et al. |
| 5,344,421 A | 9/1994 | Crook |
| 5,360,452 A | 11/1994 | Engelhardt et al. |
| 5,364,399 A | 11/1994 | Lowery et al. |
| 5,397,364 A | 3/1995 | Kozak et al. |
| 5,423,826 A | 6/1995 | Coates et al. |
| 5,458,638 A | 10/1995 | Kuslich et al. |
| 5,458,641 A | 10/1995 | Jimenez |
| 5,486,176 A | 1/1996 | Hildebrand et al. |
| 5,522,899 A | 6/1996 | Michelson |
| 5,534,027 A | 7/1996 | Hoderek |
| 5,534,032 A | 7/1996 | Hodorek |
| 5,549,612 A | 8/1996 | Yapp et al. |
| 5,571,198 A | 11/1996 | Drucker et al. |
| 5,578,034 A | 11/1996 | Estes |
| 5,601,553 A | 2/1997 | Trebing et al. |
| 5,645,606 A | 7/1997 | Ochy et al. |
| 5,681,311 A | 10/1997 | Foley et al. |
| 5,713,900 A | 2/1998 | Benzel et al. |
| 5,725,580 A | 3/1998 | Cloutier et al. |
| 5,741,258 A | 4/1998 | Klaue et al. |
| 5,782,929 A | 7/1998 | Sederholm |
| 5,888,205 A | 3/1999 | Pratt et al. |
| 5,904,683 A | 5/1999 | Pohndorf et al. |
| 5,911,758 A | 6/1999 | Ochy et al. |
| 5,935,174 A | 8/1999 | Dye |
| 5,951,557 A | 9/1999 | Luter |
| 5,951,558 A * | 9/1999 | Fiz .................. 606/70 |
| 5,954,722 A | 9/1999 | Bono |
| 5,964,762 A | 10/1999 | Biedermann et al. |
| 6,017,345 A | 1/2000 | Richelsoph |
| 6,036,697 A | 3/2000 | DiCaprio |
| 6,106,557 A | 8/2000 | Robioneck et al. |
| 6,129,730 A | 10/2000 | Bono et al. |
| 6,129,770 A | 10/2000 | Deutz et al. |
| 6,139,550 A * | 10/2000 | Michelson .................. 606/69 |
| 6,152,927 A | 11/2000 | Farris et al. |
| 6,159,213 A | 12/2000 | Rogozinski |
| 6,193,720 B1 | 2/2001 | Yuan et al. |
| 6,193,721 B1 | 2/2001 | Michelson |
| 6,206,882 B1 | 3/2001 | Cohen |
| 6,224,602 B1 | 5/2001 | Hayes |
| 6,228,085 B1 | 5/2001 | Theken et al. |
| 6,235,033 B1 | 5/2001 | Brace et al. |
| 6,235,034 B1 * | 5/2001 | Bray .................. 606/71 |
| 6,241,731 B1 | 6/2001 | Fiz |
| 6,258,089 B1 | 7/2001 | Campbell et al. |
| 6,261,291 B1 | 7/2001 | Talaber et al. |
| 6,273,889 B1 | 8/2001 | Richelsoph |
| 6,290,703 B1 | 9/2001 | Ganem |

* cited by examiner

BONE PLATE ASSEMBLY INCLUDING A SCREW RETAINING MEMBER

FIELD OF THE INVENTION

The present invention is directed to a bone plate assembly including a bone plate, bone screws received in apertures in the bone plate, and a screw retaining member attached to the bone plate which covers at least a portion of the bone screws. When bone screws have been received by the bone plate and inserted into bone and/or tissue, the bone plate assembly can be used to fuse anatomical structures together, such as adjoining bones, or to heal a fracture in bone.

BACKGROUND OF THE INVENTION

The bones and connective tissue of an adult human spinal column consist of more than twenty discrete bones coupled sequentially to one another by a tri-joint complex. The complex consists of an anterior disc and two posterior facet joints. The anterior discs of adjacent bones are cushioned by cartilage spacers referred to as intervertebral discs. The bones of the spinal column are categorized as: cervical, thoracic, lumbar, or sacral. The cervical portion of the spine which comprises the top of the spine up to the base of the skull, includes the first seven vertebrae. The intermediate twelve bones are thoracic vertebrae, and connect to the lower spine comprising the five lumbar vertebrae. The base of the spine is a sacral bones (including the coccyx).

The spinal column of bones is a highly complex anatomical structure as evidenced by the sophisticated interaction between the bones which comprise it. Furthermore, the spinal column houses and protects critical elements of the nervous system. Despite its complexity, the spine is a highly flexible structure, capable of a high degree of curvature and twist in nearly every direction.

Various types of problems can affect the structure and function of the spinal column. Such problems can be based on degenerative conditions of the intervertebral disc or the articulating joints, or trauma to the disc, bone, or ligaments supporting the spine. Other problems include tumor or infection. In addition, congenital or acquired deformities can cause abnormal angulation or slippage of the spine. Slippage (spondylolisthesis) anterior of one vertebral body on another can cause compression of the spinal cord or nerves. Patients who suffer from one or more of these conditions often experience extreme and debilitating pain, and can sustain permanent neurologic damage if the conditions are not treated appropriately.

One technique of treating these disorders is known as surgical pathrodisis of the spine. This can be accomplished by removing the intervertebral disc and replacing it with bone and immobilizing the spine to allow the eventual fusion or growth of the bone across the disc space to connect the adjoining vertebral bodies together. The stabilization of the vertebrae to allow fusion is often assisted by a surgically implanted device to hold the vertebral bodies in proper alignment and allow the bone to heal, much like placing a cast on a fractured bone. Such techniques have been effectively used to treat the above described conditions and in most cases these techniques are effective at reducing the patient's pain and preventing neurologic loss of function. However, there are disadvantages to the present stabilization devices and to the available tools to implant them.

The spinal fixation device should permit partial sharing of the weight of the vertebral bodies across the bone graft site. Bone will not heal if it is stress shielded from all weight bearing. The fixation device needs to allow for this weight sharing along with the micromotion that happens during weight sharing until the fusion is complete, often for a period of three to six months or longer, without breakage. The device must be strong enough to resist collapsing forces or abnormal angulation during the healing of the bone. Loss of alignment during healing can adversely affect the recovery. The device must be secure in its attachment to the spine to prevent migration of the implant or back out of the screws from the bone which could result in damage to the structures surrounding the spine, causing severe and potentially life threatening complications. The device must be safely and consistently implanted without damage to the patient.

The conventional method of installing bone screws entails drilling a hole, tapping the hole and threading the bone screw into the bone. To drill the hole a guide is held next to or attached to the plate. A drill is inserted into the guide and the hole drilled into the bone. The guide is removed and a tap is threaded through the hole attempting to follow the same angle as the drill hole. Caution must be used to prevent the sharp edges of the tap from damaging surrounding tissues or in creating too large a tap hole by toggling the handle of the tap. This will reduce the security of the screw bite into the bone and increases the likelihood of screw pullout. After tapping, the screw must be guided at the proper angle into the hole that has been created, as inadvertent misalignment can reduce pullout strength or result in damage to surrounding nerves or arteries.

Genetic or developmental irregularities, trauma, chronic stress, tumors and disease, however, can result in spinal pathologies which either limit this range of motion, or which threatens the critical elements of the nervous system housed within the spinal column. A variety of systems have been disclosed in the art which achieve this immobilization by use of a surgical implant. It is known that with cervical plates, the screw head may be provided with an arcuate shape, and the plate may be provided with a recess having a complimentary shape that receives the shape of the head. In this arrangement, the head and plate share load bearing responsibilities over an enlarged surface area. Further, since each of the head and recess have arcuate surfaces, the screw shaft is able to rotate in an arcuate path relative to its longitudinal axis. For instance, as shown in U.S. Pat. No. 5,534,027 at col. 4 lines 18–19 and FIG. 5, it is possible for "axis "A" of the screw 10 to be at an angle "AA" to axis "B" of the hole 31.

SUMMARY OF THE INVENTION

The present invention is directed to a bone plate assembly including a bone plate having apertures through which bone screws are received and a screw retaining member that covers at least a portion of the bone screws. The screw retaining member is provided with an aperture that receives a member such as a screw which fixes the screw retaining member to the bone plate. The bone plate assembly of the present invention can be fastened to at least two bones, or at least two portions of bones, in order to facilitate the healing process. The bone plate is provided with apertures through which bone screws are received and fitted into drill holes, in order to fasten the plate to bone.

In one embodiment, the screw holes in the bone plate are not provided with uniform dimensions. For example, in one embodiment, the size of a dimension D1 of the apertures is greater than the size of a dimension D2 of the apertures. In another embodiment, D1 corresponds to the length dimension of the aperture and D2 corresponds to the width dimension of the aperture. In yet another embodiment, length dimension D1 of the aperture runs in the same direction as length dimension D1 of the bone plate. The bone screws which are inserted into the apertures, which have a screw head, and a shaft, possess dimensions that permit the screw to move in the D1 dimension.

In yet a further embodiment, the aperture of the screw retaining member is not provided with uniform dimensions. For example, in one embodiment, the size of a dimension D1 of the apertures in the screw retaining members is greater than the size of a dimension D2 of the apertures in the screw retaining members. In another embodiment, D1 corresponds to the length dimension of the apertures and D2 corresponds to the width dimension of the apertures. In yet another embodiment, length dimension D1 of the apertures in the screw retaining members runs in the same direction as length dimension D1 of the apertures that receive the bone screws. In yet another embodiment, length dimension D1 of the apertures in the screw retaining members runs in the same direction as length dimension D1 of the of the apertures that receive the bone screws, and in the same direction as length dimension D1 of the bone plate. The screws which are inserted into the apertures in the screw retaining members and fix it to the bone plate possess a smaller dimension in the D1 direction the screw retaining member is able to move with respect to the D1 dimension of its aperture.

In a further embodiment, the screw retaining member is in contact with the bone screw when the screw retaining member is fixed to the bone plate. In another embodiment, the screw retaining member, or a portion thereof, resides in a position that permits it to contact the bone screw when the bone screw moves within the bone plate. Accordingly, in these embodiments, the present invention permits the screws and screw retaining members to move in at least one direction. This is desirable, as it allows the locations of the screws and screw retaining members to shift in accordance with the shifting loads placed upon the vertebrae to which the plate is anchored. In yet another embodiment, the screw retaining member is spaced away from the bone plate in a position prevents the screw retaining member from backing out of the bone plate, which could happen if the screws unloosened from the bone in which they were inserted.

Yet another embodiment of the present invention is directed to a bone plate assembly for implantation in an anatomical body having a bone plate having apertures and bone screws received in the apertures, a screw retaining member having an aperture for receiving a member that fixes the screw retaining member to the bone plate, the bone plate having a location for receiving the member that fixes the screw retaining member to the bone plate, the screw retaining member covering at least a portion of the bone screw, wherein when the screw retaining member is fixed to the bone plate, a gap is present between the bone plate and screw retaining member in the region between the apertures for the bone screws and the location for receiving the member that fixes the screw retaining member to the bone plate, and further, the screw retaining member rests upon the bone plate in at least one bone plate location. In yet another embodiment, the screw retaining member rests upon the bone plate at a sidewall of the apertures for receiving the bone screws. In yet a further embodiment, the bone plate is provided with a relatively flat region between the apertures for the bone screws and the location for receiving the member that fixes the screw retaining member to the bone plate. In yet a further embodiment, the screw retaining member is provided with an arcuate region between the apertures for the bone screws and the location for receiving the member that fixes the screw retaining member to the bone plate. In a yet further embodiment, the screw retaining member is provided with an arcuate region between the apertures for the bone screws and the location for receiving the member that fixes the screw retaining member to the bone plate, and the bone plate is provided with a relatively flat region between the apertures for the bone screws and the location for receiving the member that fixes the screw retaining member to the bone plate.

DETAILED DESCRIPTION OF THE PREFERRED EMBODIMENT

Figure 1:
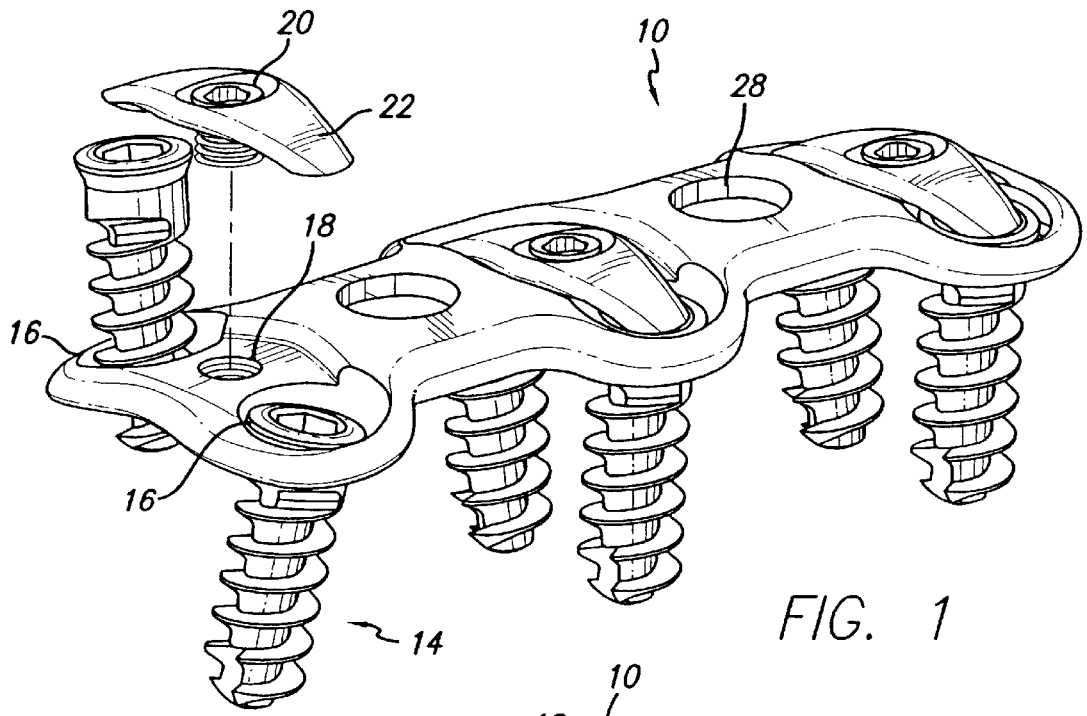
FIG. 1 is a perspective view of an embodiment of the invention.

FIG. 1 presents a perspective view of the structure 10 of the present invention in which bone plate 12 is shown with bone screws 14 inserted into the apertures 16 within the plate 12. The bone plate 12 is further provided with apertures 18 located between the apertures 16, which receive a screw in order to fix the screw retaining member 22 in place.

Figure 2:
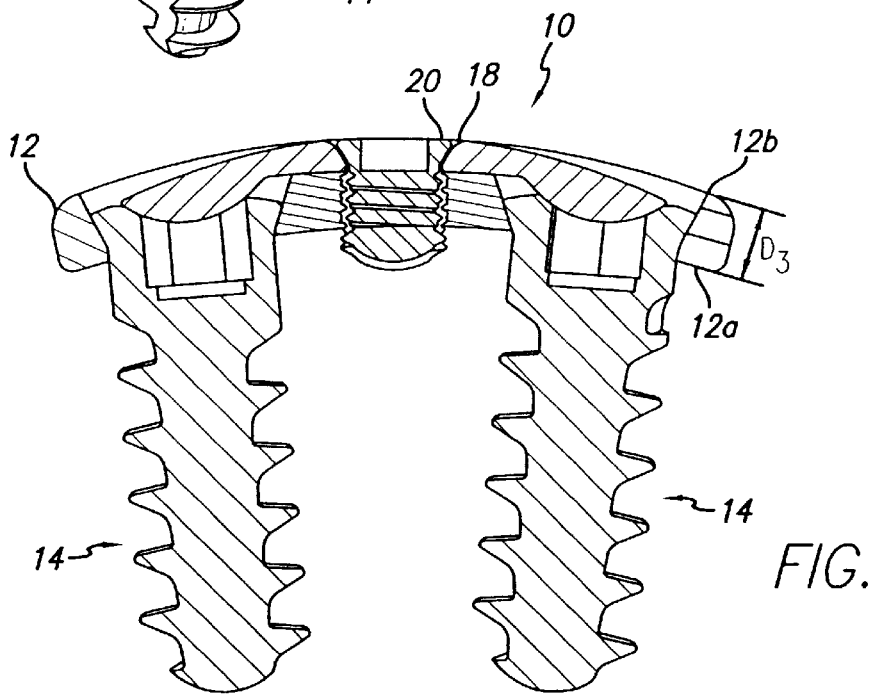
FIG. 2 is an end view of an embodiment of the present invention.
Figure 11A:
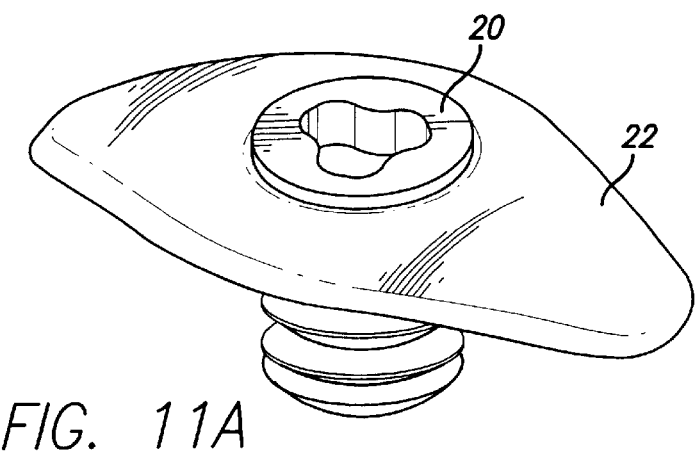
FIG. 11 shows an additional embodiment of the screw retaining member.
Figure 11B:
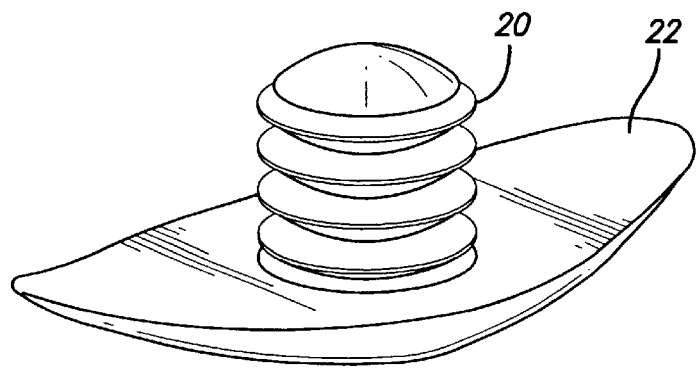

As best viewed in FIG. 2, the bone plate has an accurate shape which mirrors the shape of the bone structure against which it is placed. In this Figure and in FIG. 7, the screw retaining member 22 has hemispherical surfaces 50 at the edges 25 that contact the heads of the bone screws. With this arrangement, the screw retaining member 22 shares some of the load borne by the bone screws, which possibly may reduce or eliminate the occurrence of load shear upon the screws. Alternatively, the hemispherical surfaces can be omitted. See FIG. 11.

Figure 9:
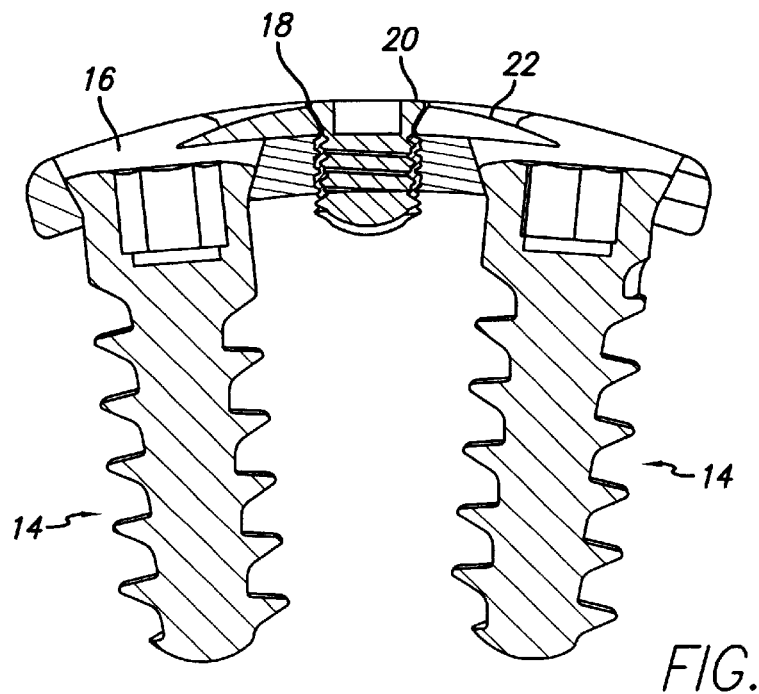
FIG. 9 is an end view of another embodiment of the present invention.

FIG. 9 shows an arrangement in which the screw head and screw retaining member are not in contact with each other. The screw retaining member is situated over the bone screw, sufficiently close thereto to prevent the screw from backing out of the bone in which it is inserted. In this arrangement the tapered shape of the screw retaining member, which will be described below, allows the bone screw to be inserted at variety of angles, including perpendicular to the surface of the bone and at, for example, angles of 5 degrees and 10 degrees to the shaft of the screw when the screw is inserted perpendicular to the surface of the bone.

Figure 3:
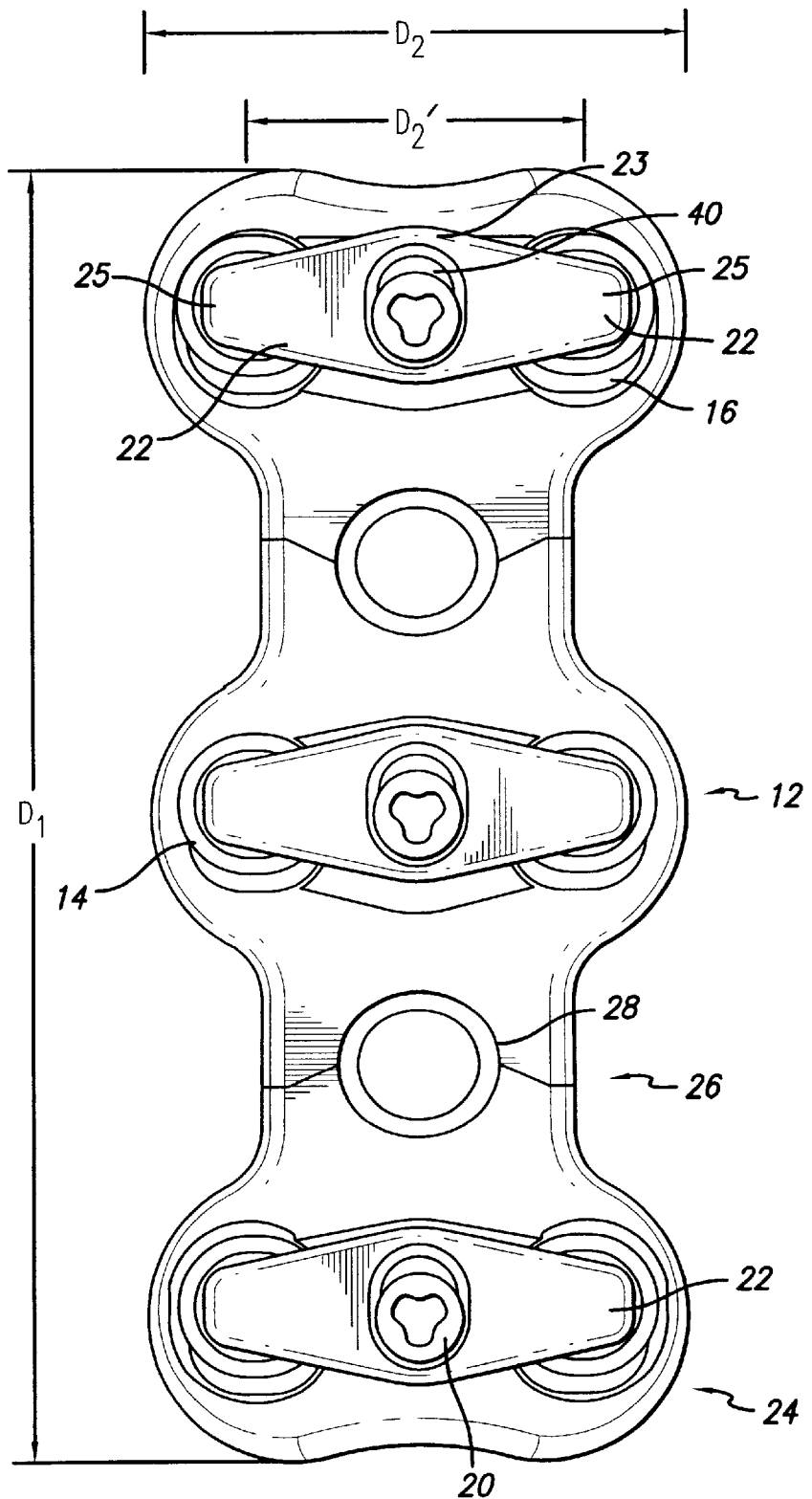
FIG. 3 is a top plan view of an embodiment of the present invention.

Turning now to FIG. 3 which shows a top plan view of the bone plate, it can be seen that regions 24 in which the bone screws 16 are inserted is sized greater in dimension D2 than in the size of corresponding dimension D2' of the intermediate regions 26.

The plate 12 is provided with a first dimension D1, a second dimension D2 (FIG. 3), and a third dimension D3 (FIG. 2). While as shown in the disclosed embodiments, D1 corresponds to length dimension L, D2 corresponds to width dimension W, and D3 corresponds to depth dimension, or thickness T, this may not always be the case. That is, for example, D1 may not always correspond to L, it may in other cases correspond to some other dimension, such as W. For this reason, the present disclosure will hereinafter use only the generic terminology with the understanding that what the terminology denotes is determined on a case-by-case basis.

Figure 4A:
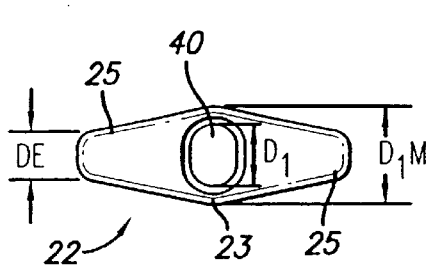
FIG. 4A is a top plan view of an screw retaining member.
Figure 4B:
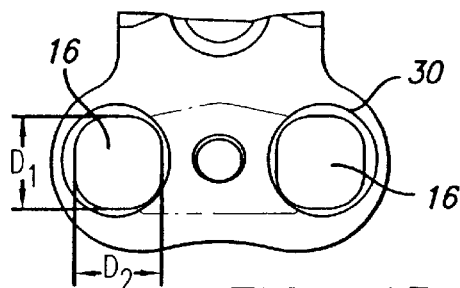
FIG. 4B is a top plan view of a portion of a bone plate.
Figure 5:
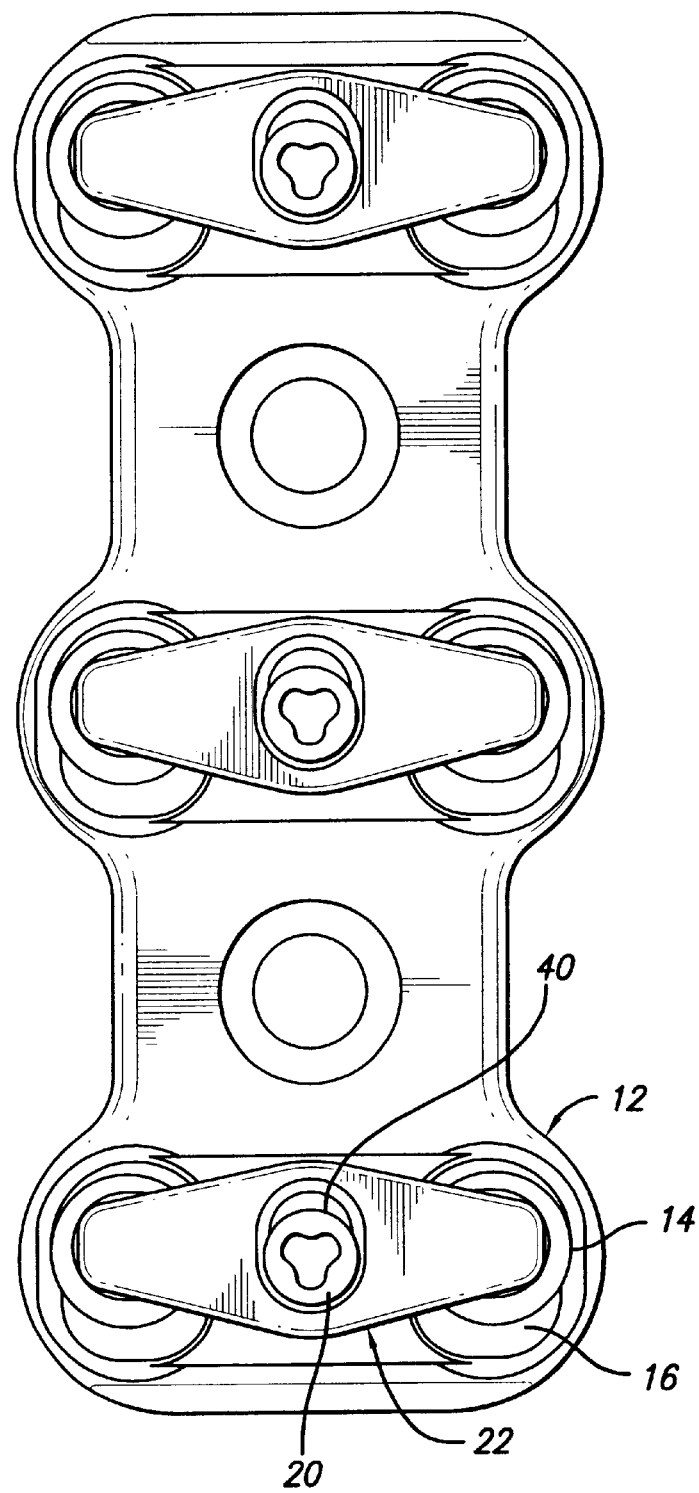
FIG. 5 is a further top plan view of an embodiment of the present invention.

Referring to FIG. 4B, dimension D1 of the apertures 16 in the bone plate 12 are sized greater than dimension D2 of the apertures 16. The size of at least one of the corresponding dimensions D1, D2 of the shaft of the bone screw and/or screw head are smaller than the dimension D1 of the aperture 14. (It should be understood that with respect to screws, often there is symmetry, in which case D1=D2, further in which case both dimensions are smaller than the dimension D1 of the aperture 16.) Therefore, when screws are within the apertures 16, open space is present within the aperture on at least in the direction in which D1 extends. This enables the screw to move in the direction of the D1 dimension. In one embodiment D1 runs in the direction of the length dimension of the bone plate. This arrangement is shown in FIG. 5.

The intermediate regions are provided with apertures 28. These apertures provide a view of the underlying bone structure, and further, provide a location for the bone graft.

As best seen in FIG. 2, the sidewalls 30 defining the aperture 16 are provided with a tapered profile, in which the cross sectional area of aperture 16 at the bottom 12a of the plate 12 is smaller than the cross sectional area of the aperture 16 at the top 12b of the plate 12. Over dimension D3, the cross sectional area of the aperture 16 gradually increases from the bottom plate side 12a to the top plate side 12b. This can be effected by gradually increasing the size of dimension D1 and/or the size of dimension D2 over the traversal of dimension D3 from the bottom of 12a to the top of plate 12b.

Figure 6:
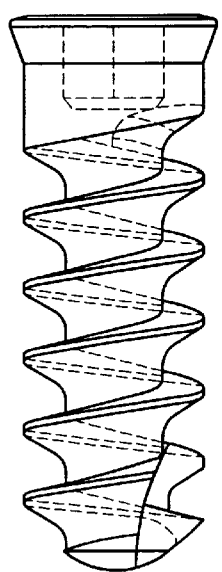
FIG. 6 is a side elevational view of an bone screw used in the embodiments of the present invention.

A screw suitable for use in conjunction with the bone plate 12 is shown in FIG. 6. Screw 14 is shown having a head 30 connected to a shaft 32. The shaft is provided with threads that permit it to be inserted into an anatomical body, such as bone or tissue, by rotating it. The screw head is provided with a groove or slot 36 in its top surface 38, which may be key shaped or hex shaped, The screw head 36 receives the head of a screwdriver, drill, hex driver, or other device used to drive the screw into bone. These screws, as well as the bone plate 12 and screw retaining member 22 may be constructed of any material known to be suited for constructing surgical implants. To name just a few merely for exemplary purposes, such materials include titanium, cobalt chromium alloy, stainless steel, plastic materials, and bioabsorsbable materials.

A suitable screw used in joining the screw retaining member to the bone plate may be the Spiralock®, available from Spiralock Corporation, Madison Hills, Mich., USA.

A suitable screw retaining member 22 is shown in FIG. 4A. The screw retaining member 22 has a shape in which its size in the mid portion of the member 23 is greater than the size at the edges 25 of the member. That is, with reference to the previously defined orientation of the dimensions of the bone plate, the screw retaining member 22 has a dimension D1M sized greater in the mid portion 23 of the member 22 than the dimension D1E at the edges 25 of the member 23. Dimension D1 of the screw retaining member gradually decreases from the mid portion 23 to the edges 25 of the member, so that the screw retaining member has a tapered wing-like appearance. The edges cover at least a portion of the bone screws. In one embodiment, the edges 25 of the screw retaining member reside over the groove in the same plane as the top surface 40 of the bone screw 12. In one embodiment, the edges 25 of the screw retaining member reside in the groove in the same plane as the top surface 40 of the bone screw 12. In yet another embodiment, the screw retaining member is in contact with the bone screw 12.

Still with reference to FIG. 4A, the screw retaining member 22 is provided with an aperture 40 located in its mid portion 23. The aperture 40 of the screw retaining member 22 is not provided with uniform dimensions. Dimension D1 of the apertures 40, in the screw retaining member 22 is shown as greater in size than dimension D2 of the aperture 16. The size of at least one of the corresponding dimensions D1, D2 of the screw are smaller than the dimension D1 of the aperture 40. (It should be understood that with respect to screws, often there is symmetry, in which case D1=D2, further in which case both dimensions are smaller than the dimension D1 of the aperture 40.) Screws 20 are received within the apertures 40 and received within aperture 18 of the bone plate, thereby joining the screw retaining member to the bone plate 12.

Figure 7:
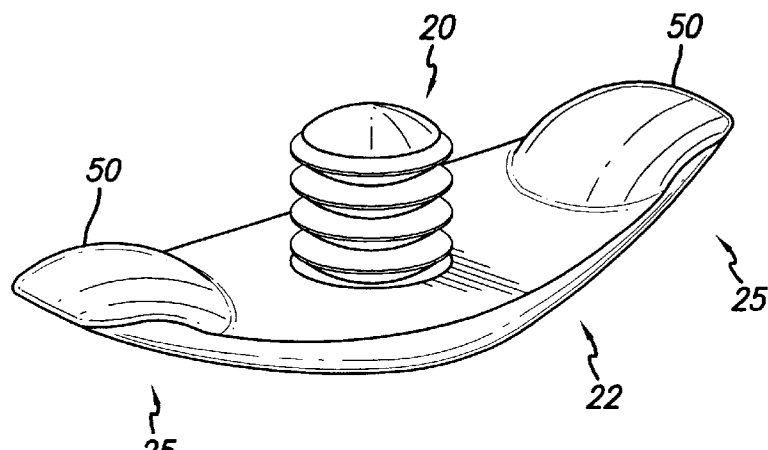
FIG. 7 shows an additional embodiment of the screw retaining member.
Figure 8:
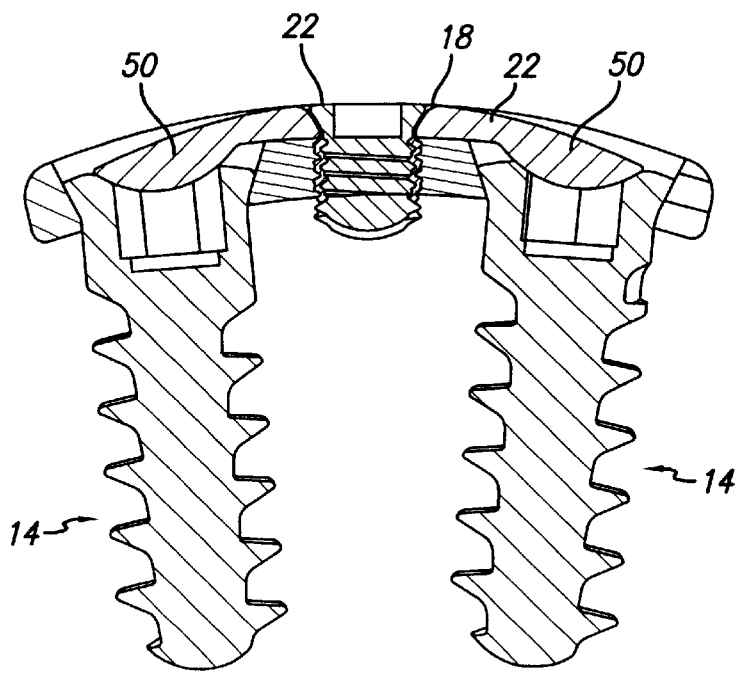
FIG. 8 shows an embodiment of an assembly showing the screw retaining member of FIG. 7.

An additional embodiment of the screw retaining member are shown in FIG. 7. Here, the edges 25 of the screw retaining member are provided with bulbous protrusions that engage with and reside in the groove or apertures of the bone screws. An embodiment of an assembly showing this arrangement is shown in FIG. 8. When the screw received in aperture 40 of the screw retaining member is tightened, the screw retaining member can be brought into compression against the bone screws.

When the assembly is implanted in an anatomical body, such as when bone screws are inserted though the bone plate apertures and implanted in adjoining vertebrae, the bone screws can move linearly within the apertures in response to a load placed on the vertebrae. In other words, when the spinal column is compressed, the screws of the implant are capable of moving in a linear direction in response to the compression. The movement in a linear direction is effected by the screws 14 moving through the apertures 16 in the bone plate 12. As the screws 14 move, the edges of the retaining member 22 catch the top surface 38 of the screw, and accordingly, the retaining member 22 moves linearly along with the screw 14, since the aperture through which the screw is positioned has the same dimensional orientation as the dimensional orientation of the apertures through which the bone screws are placed (i.e., the longer dimensions D1 of the apertures 16, 40 in the bone plate 12 and screw retaining member 22 are oriented with each other). In this arrangement, the retaining member shoulders part of the load of compression and helps the bone screws maintain a linear orientation under compression.

Figure 10:
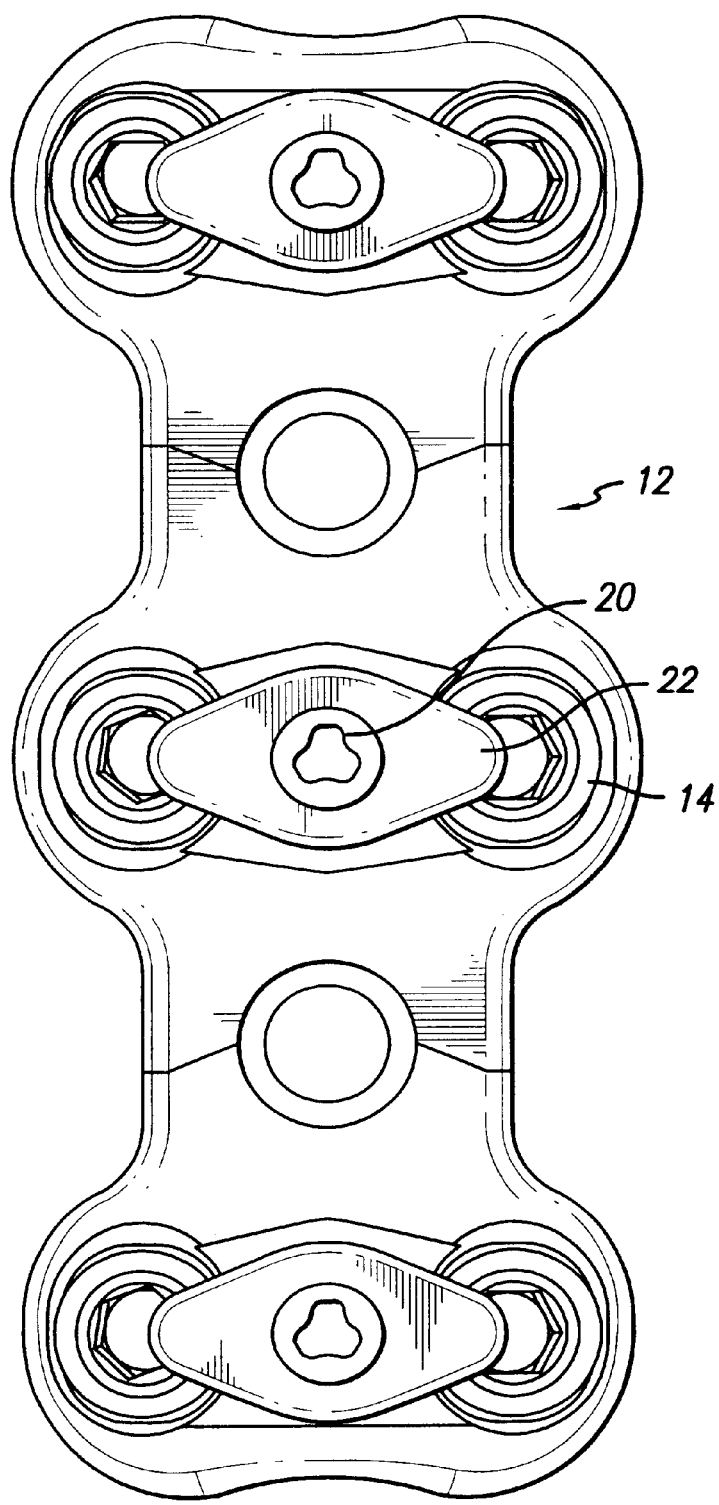
FIG. 10 is a top plan view of another embodiment of the present invention.

In a further embodiment, shown in FIGS. 9 and 10, the screw retaining member does not contact the screw head, and there is a gap between the screw retaining member and the top surface of the bone screw. The screw retaining member is situated over the bone screw, sufficiently close thereto to prevent the screw from backing out of the bone in which it is inserted. In this arrangement the tapered shape of the screw retaining member, which will be described below, allows the bone screw to be inserted at variety of angles, including perpendicular to the surface of the bone and at, for example, angles of 5 degrees and 10 degrees to the shaft of the screw when the screw is inserted perpendicular to the surface of the bone. In this arrangement, the aperture of the screw retaining member which receives the set screw can be dimensioned in a way that the set screw fills the entirety of the aperture in which the set screw is received, thereby not allowing for movement of the screw retaining member.

Figure 12:
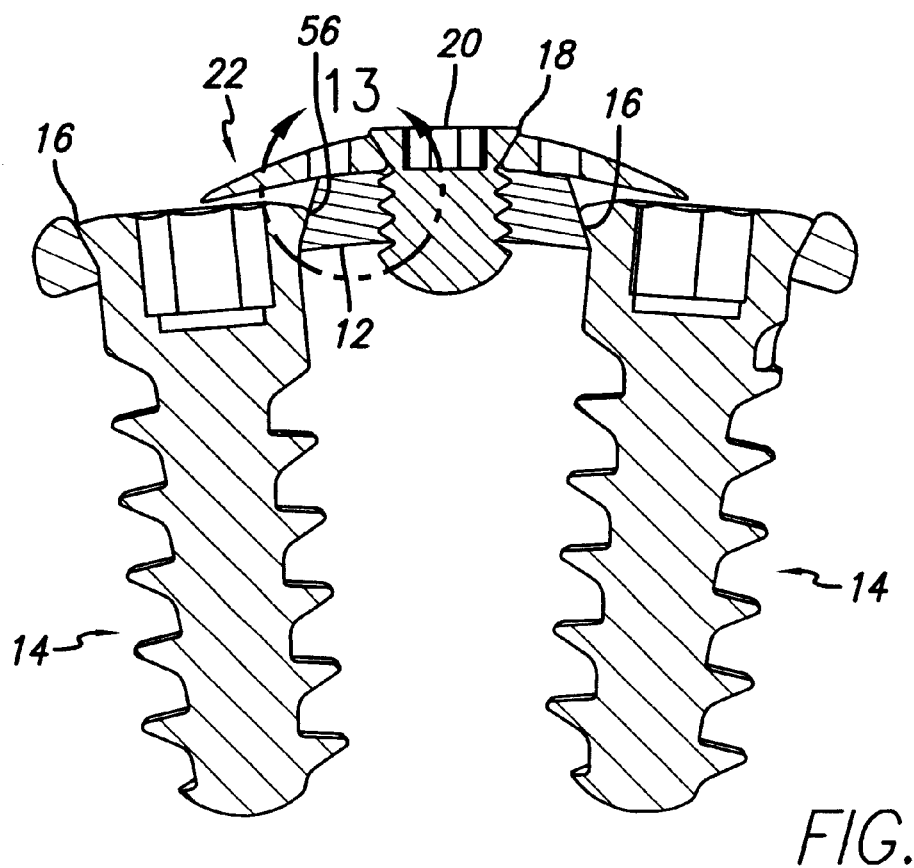
FIG. 12 shows an end view of yet another embodiment of the present invention.
Figure 13:
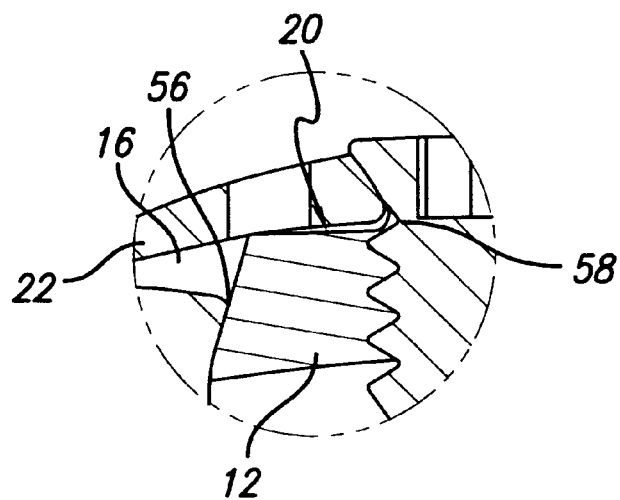
FIG. 13 is a perspective view of features of the FIG. 12 embodiment.

In yet a further embodiment, shown in FIGS. 12 and 13, the upper surface 52 of the bone plate in the areas between the apertures and 16 is flat, although the overall shape of the bone plate when viewed from its ends, is arcuate. The bottom surface 54 of the screw retaining member 22 in this area is arcuate, so that along the segment between the apertures 18 and 16 the screw retaining member 22 and the bone plate are in only at the sidewall 56 of the aperture 16.

When set screw 20 is tightened, fixing the screw retaining member in place, the application of a downward force in the midportion of the screw retaining member causes the screw retaining member to move into the gap 58 between the bone plate and screw retaining member. Movement of the screw retaining member causes the edges of the screw retaining member to flex upward. With this arrangement, the set screw 20 is prevented from backing out.

Numerous modifications and variations of the present invention are possible in light of the above teachings. It is evident that variations on the present invention may be constructed, which, in accordance with controlling law, are still subject to the claims written in view of the preceding disclosure.

We claim:

1. A bone plate assembly for implantation in an anatomical body, comprised of: a bone plate having apertures sized greater in at least one dimension than bone screws received in the apertures, a screw retaining member having an aperture for receiving a member that fixes the screw retaining member to the bone plate, the screw retaining member covering at least a portion of the bone screws, wherein the aperture in the screw retaining member is asymmetrically shaped and sized greater in at least one dimension than a member received within the aperture fixing the screw retaining member to the bone plate, wherein when the assembly is implanted in an anatomical body, the bone screws and screw retaining member are movable in a path corresponding to the dimensions defined by the respective apertures.

2. The bone plate assembly of claim 1 wherein the at least one dimension of the apertures in the bone plate and the screw retaining member extend in the direction of a first dimension of the bone plate, the bone plate also having a second dimension, wherein the first dimension of the bone plate is sized greater than the second dimension of the bone plate.

3. The bone plate assembly of claim 1 wherein the at least one dimension of the apertures in the bone plate and the screw retaining member corresponds to the length dimension and the apertures further possess a second dimension which corresponds to the width dimension.

4. The bone plate assembly of claim 2 wherein the at least one dimension of the apertures in the bone plate and the screw retaining member extend in the direction of a first dimension of the bone plate, which also has a second dimension, wherein the first dimension of the bone plate is sized greater than the second dimension of the bone plate, and wherein the first dimension of the bone plate, the at least one dimension of the apertures in the bone plate, and the at least one dimension of the aperture in the screw retaining member correspond to the length dimension, and the second dimension of the bone plate, a second dimension of the apertures in the bone plate, and a second dimension of the aperture in the screw retaining member correspond to the width dimension.

5. The assembly of claim 1 wherein the screw retaining member has a midportion where the aperture is located and edge portions on the sides of the midportion which cover the bone screws, wherein the screw retaining member extends in a first and second dimension, wherein the size of the first dimension is greater in the midportion of the screw retaining member than size of the first dimension at the edges.

6. The assembly of claim 5 wherein the bone screw has a top surface having a groove.

7. The assembly of claim 6 wherein the edge portions of the screw retaining member resides over the groove in the same plane as the top surface of the bone screw.

8. The assembly of claim 6 wherein the edge portions of the screw retaining member reside in the groove on the top surface of the bone screw.

9. The assembly of claim 8 wherein the edge portions of the screw retaining member are provided with protrusions that reside in the groove on the top surface of the bone screw.

10. The assembly of claim 6 wherein the screw retaining member contacts the top surface of the bone screw.

11. The assembly of claim 9 wherein the screw retaining member contacts the top surface of the bone screw.

12. The assembly of claim 1 wherein the apertures on the bone screw are located in a recessed portion of the bone plate.

13. A bone plate assembly for implantation in an anatomical body, comprised of: a bone plate having apertures with a first dimension sized greater than a second dimension; bone screws received in the apertures, a screw retaining member having an aperture for receiving a member that fixes the bone plate and covers at least a portion of the bone screw, the bone plate having a location for receiving the member that fixes the screw retaining member to the bone plate, wherein the aperture in the screw retaining member has first and second dimensions, wherein the first dimension is greater in size than the second dimension, wherein when the assembly is implanted in an anatomical body the bone screws and screw retaining member are movable in a path corresponding to the dimensions defined by the respective apertures.

14. The bone plate assembly of claim 13 wherein the first dimension of the apertures in the bone plate and the screw retaining member extend in the direction of a first dimension of the bone plate, the bone plate also having a second dimension, wherein the first dimension of the bone plate is sized greater than the second dimension of the bone plate.

15. The bone plate assembly of claim 13 wherein the first dimension of the apertures in the bone plate and the screw retaining member corresponds to the length dimension and the second dimensions of the apertures in the bone plate and the screw retaining member corresponds to the width dimension.

16. The bone plate assembly of claim 14 wherein the first dimension of the apertures in the bone plate and the screw retaining member extend in the direction of a first dimension of the bone plate, which also has a second dimension, wherein the first dimension of the bone plate is sized greater than the second dimension of the bone plate, and wherein the first dimension of the bone plate, the first dimension of the apertures in the bone plate, and the first dimension of the aperture in the screw retaining member correspond to the length dimension, and the second dimension of the bone plate, the second dimension of the apertures in the bone plate, and the second dimension of the aperture in the screw retaining member correspond to the width dimension.

17. The assembly of claim 15 wherein the screw retaining member has a midportion where the aperture is located and edge portions on the sides of the midportion which cover the bone screws, wherein the screw retaining member extends in a first and second dimension, wherein the size of the first dimension is greater in the midportion of the screw retaining member than size of the first dimension at the edges.

18. The assembly of claim 17 wherein the bone screws have a top surface having a groove.

19. The assembly of claim 18 wherein the edge portions of the screw retaining member resides over the groove in the same plane as the top surface of the bone screws.

20. The assembly of claim 18 wherein the edge portions of the screw retaining member reside in the groove on the top surface of the bone screws.

21. The assembly of claim 18 wherein the screw retaining member contacts the top surface of the bone screws.

22. The assembly of claim 13 wherein the apertures on the bone screws are located in a recessed portion of the bone plate.

23. A screw retaining member fixable to a bone plate, wherein the screw retaining member is comprised of a midportion where the screw retaining member is fixed to the bone plate, and edge portions on the sides of the midportion, wherein the screw retaining member extends in a first and second dimension, wherein the size of the first dimension is greater in the midportion of the screw retaining member than the size of the first dimension at the edges.

24. The screw retaining member of claim 23 wherein the size of the first dimension decreases gradually from the midportion of the screw retaining member to the edges.

25. The screw retaining member of claim 23 wherein the screw retaining member is provided with a set screw that fixes the screw retaining member to the bone plate.

26. A bone plate assembly for implantation in an anatomical body, comprised of: a bone plate having apertures and bone screws received in the apertures, a screw retaining member having an aperture for receiving a member that fixes the screw retaining member to the bone plate, the bone plate having a location for receiving the member that fixes the screw retaining member to the bone plate, the screw retaining member covering at least a portion of the bone screw, wherein when the screw retaining member is fixed to the bone plate, a gap is present between the bone plate and screw retaining member in the region between the apertures for the bone screws and the location for receiving the member that fixes the screw retaining member to the bone plate, and further, the screw retaining member rests upon the bone plate at a sidewall of the apertures for receiving the bone screws.

27. The bone plate assembly of claim 26 wherein the bone plate is provided with a relatively flat region between the apertures for the bone screws and the location for receiving the member that fixes the screw retaining member to the bone plate.

28. The bone plate assembly of claim 26 wherein the screw retaining member is provided with an arcuate region between the apertures for the bone screws and the location for receiving the member that fixes the screw retaining member to the bone plate.

29. The bone plate assembly of claim 28 wherein the screw retaining member is provided with an arcuate region between the apertures for the bone screws and the location for receiving the member that fixes the screw retaining member to the bone plate.

30. A bone plate assembly for implantation in an anatomical body, comprised of: a bone plate having apertures sized greater in at least one dimension than bone screws received in the apertures, a screw retaining member having an aperture for receiving a member that fixes the screw retaining member to the bone plate, the screw retaining member covering at least a portion of the bone screws, wherein the aperture in the screw retaining member is asymmetrically shaped and is sized greater in at least one dimension than a member received within the aperture fixing the screw retaining member to the bone plate, wherein when the assembly is implanted in an anatomical body, the bone screws and screw retaining member slide relative to the bone plate in a path corresponding to the dimensions defined by the respective apertures.

31. A bone plate assembly for implantation in an anatomical body, comprised of: a bone plate having apertures with a first dimension sized greater than a second dimension; bone screws received in the apertures, a screw retaining member having an aperture for receiving a member that fixes the bone plate and covers at least a portion of the bone screw, the bone plate having a location for receiving the member that fixes the screw retaining member to the bone plate, wherein the aperture in the screw retaining member has first and second dimensions, wherein the first dimension is greater in size than the second dimension, wherein when the assembly is implanted in an anatomical body the bone screws and screw retaining member slide relative to the bone plate in a path corresponding to the dimensions defined by the respective apertures.

* * * * *